(12) United States Patent
Gilo et al.

(10) Patent No.: US 7,846,480 B2
(45) Date of Patent: Dec. 7, 2010

(54) MANUFACTURE OF STRONG, LIGHTWEIGHT CARRIER GRANULES

(75) Inventors: Yechiel Gilo, Greensboro, NC (US);
Steven G. Myers, Mocksville, NC (US)

(73) Assignee: Cycle Group, Inc., Mocksville, NC (US)

( * ) Notice: Subject to any disclaimer, the term of this patent is extended or adjusted under 35 U.S.C. 154(b) by 1358 days.

(21) Appl. No.: 11/335,556

(22) Filed: Jan. 20, 2006

(65) Prior Publication Data

US 2006/0121075 A1     Jun. 8, 2006

Related U.S. Application Data

(63) Continuation-in-part of application No. 10/813,227, filed on Mar. 31, 2004, now abandoned.

(51) Int. Cl.
*A61K 9/14* (2006.01)
*A61K 9/50* (2006.01)

(52) U.S. Cl. .................. 424/489; 424/499; 424/500

(58) Field of Classification Search ................ None
See application file for complete search history.

(56) References Cited

U.S. PATENT DOCUMENTS

| | | | |
|---|---|---|---|
| 5,019,564 A | 5/1991 | Lowe et al. | |
| 5,078,779 A | 1/1992 | Van de Walle et al. | |
| 5,242,690 A | 9/1993 | Moechnig | |
| 5,843,203 A * | 12/1998 | Lindsay et al. | ................ 71/23 |
| 5,888,345 A | 3/1999 | Knapick et al. | |
| 5,970,916 A * | 10/1999 | Yoder et al. | ................ 119/173 |
| 6,030,565 A | 2/2000 | Golan | |

(Continued)

FOREIGN PATENT DOCUMENTS

WO    WO 2005/097071 A2    10/2005

OTHER PUBLICATIONS

BIODAC® composition (http://www.kadantgrantek.com/bio_property.html), (2002).

*Primary Examiner*—Humera N Sheikh
(74) *Attorney, Agent, or Firm*—Birch, Stewart, Kolasch & Birch, LLP

(57) ABSTRACT

Method for manufacturing carrier granules. The method forms a mixture comprising fibers, mineral filler, and binder. The mixture contains 32-48 weight-% wood fibers having a bulk density of less than 20 pounds per cubic foot, at least 35 weight-% of which fibers are retained on a 50-Mesh U.S. Sieve Series screen. The fibers have a moisture content of less than 15 weight-%. The mixture also contains 52-65 weight-% mineral filler having a moisture content of less than 12 weight-%. In addition, the mixture contains 3-7 weight-% binder. The mixture is agglomerated by conditioning and agglomerating it in a pin mixer to form small particles followed by agglomerating it in a disc or pan pelletizer to form substantially spherical granules. The method then dries the granules to a moisture content of less than about 5 weight-%, and screens the granules to select granules that pass through a 10-Mesh U.S. Sieve Series screen but are retained on a 40-Mesh U.S. Sieve Series screen. The carrier granules have a bulk density of less than 40 pounds per cubic foot and a Resistance to Attrition of at least 95%.

9 Claims, 2 Drawing Sheets

U.S. PATENT DOCUMENTS

| | | |
|---|---|---|
| 6,089,189 A | 7/2000 | Goss et al. |
| 6,194,065 B1 | 2/2001 | Golan |
| 6,231,660 B1 | 5/2001 | Welshimer et al. |
| 6,294,118 B1 | 9/2001 | Huber et al. |
| 6,572,920 B1 | 6/2003 | Eitan et al. |
| 6,613,138 B2 | 9/2003 | Weshimer et al. |
| 6,745,720 B2 * | 6/2004 | Rasner et al. ............... 119/172 |
| 2003/0170905 A1 | 9/2003 | Kamyshny et al. |
| 2004/0112297 A1 | 6/2004 | Rasner et al. |
| 2006/0121075 A1 | 6/2006 | Gilo et al. |
| 2007/0098752 A1 | 5/2007 | Gilo et al. |

* cited by examiner

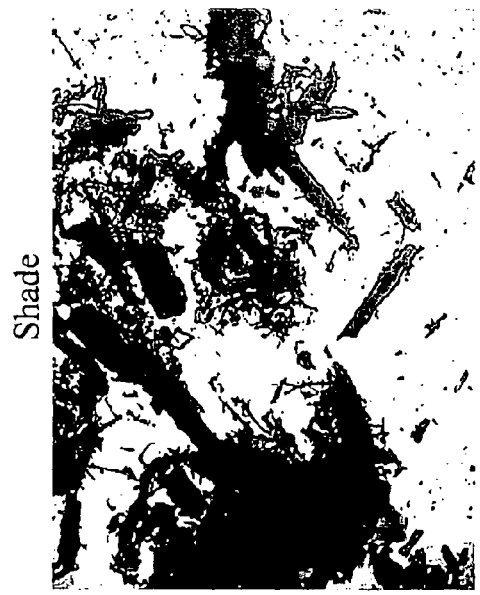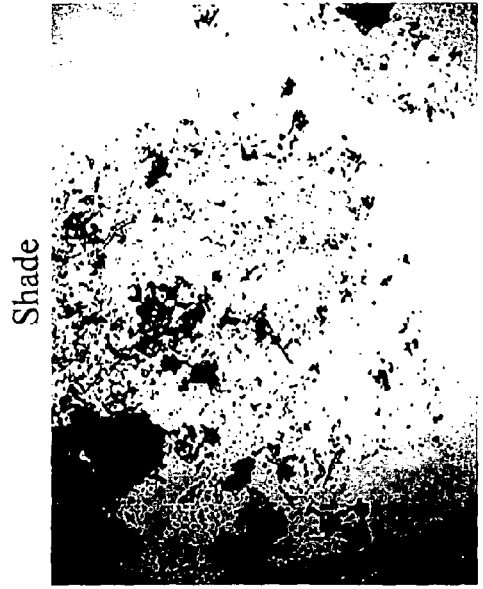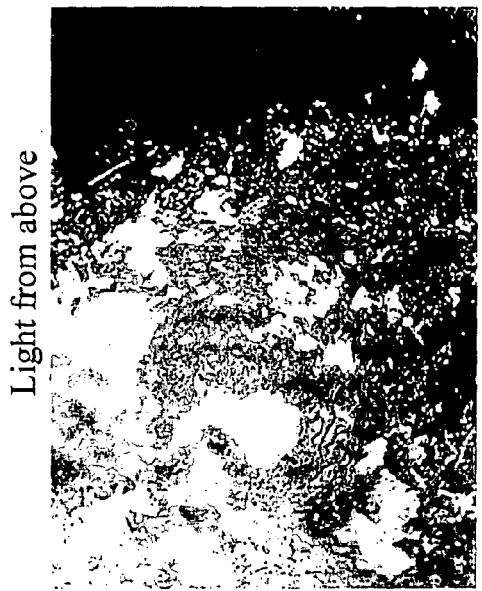
FIG.1A FIG.1B

MANUFACTURE OF STRONG, LIGHTWEIGHT CARRIER GRANULES

This application is a continuation-in-part of application Ser. No. 10/813,227, which was filed on Mar. 31, 2004 now abandoned. The entire disclosure of Ser. No. 10/813,227 is expressly incorporated by reference herein.

FIELD OF THE INVENTION

This invention relates to the manufacture of carrier granules suitable for use as carriers for herbicides, insecticides, and fungicides, for plant growth regulators, and for other biologically active compounds. The carrier granules of this invention are made of a mix of wood fibers, powdered minerals, and binder. The small particle size of these ingredients optimize their mixing within the granule, creating a homogenous structure. The unique properties of the wood fiber component herein and the innovative manufacturing method of this invention provides carrier granules that have a superior balance between strength, size, and weight.

BACKGROUND OF THE INVENTION

Manufacture granular particles are conventionally used as carriers for agricultural chemicals such as herbicides, plant growth regulators, fertilizers, etc. Various different types of granules are currently used for such applications. Patents disclosing granules include the following.

U.S. Pat. No. 5,019,564 discloses granules formed by the agitated agglomeration of slurries containing plant fibers and mineral fillers. These granules are utilized as carriers for biologically active chemical agents.

U.S. Pat. No. 5,078,779 discloses binder compositions that include reactive carbonates and reactive sulfates in combination with silicate strengthening agents and water-dispersing agents. These binders are used to carry ammonium sulfate fertilizers.

U.S. Pat. No. 5,242,690 discloses granular carrier compositions that include grain dust and a binder of calcium or sodium lignosulfonate, the compositions being useful as carriers for biologically active chemical agents.

U.S. Pat. No. 6,613,138 B2 and U.S. Pat. No. 6,231,660 B1 disclose granules that include one or more mineral components, one or more "light weight additives", and one or more water soluble binders. These patents teach that the lightweight additives should be a non-fibrous material, because fibrous material can adversely impact the dispersibility and the flow characteristics of the finished granular substrate. The terminology "light weight additive" is vague. However, the patent provides some idea of what is meant by that terminology: "The light weight additives are preferably selected from the group consisting of expanded silica, fly ash, hydrated lime, wheat flour, wood flour, ground wheat straw, cellulose and soy flour." U.S. Pat. No. 6,231,660, column 4, lines 33-36; 6,613,138, column 4, lines 46-49. The patentee explains what "wood flour" involves in the following words: "A preferred embodiment includes the use of wood flour resulting from finely milled wood particle board. The wood particle board contains approximately 10 wt % of a urea-formaldehyde resin. Another preferred embodiment includes the use of wheat straw flour resulting from finely milled wheat straw particle board. The wheat straw particle board contains a diphenylmethane diisocyanate resin." U.S. Pat. No. 6,613,138, column 4, lines 40-46; 6,231,660, column 4, lines 52-58. The Examples in the patent disclose as binders brewers condensed solubles, calcium lignosulfonate, cane molasses, beet syrup, beet molasses, hydrolyzed collagen, soy solubles, whey, sodium carbonate lignin, protein amino acids, hemicellulose extract, sodium carboxymethyl cellulose, corn starch mixed with sodium carboxymethyl cellulose, and Baka-Snak.

There is an unmet need for carrier granules that will better satisfy the needs of industry. In particular, there is a need for small, light granules, having particles in the size range 10/40 Mesh and weighing approximately, for instance, around 28 pounds per cubic foot. The carrier granules should also have a Resistance to Attrition rating of greater than 95%. While some of these characteristics are found in some currently available granules, we are unaware of any carrier granules that provide all of these characteristics at the same time. A purpose of this invention is to provide carrier granules having particles in the size range 10/40 Mesh and weighing on the order of magnitude of 28 pounds per cubic foot and having a Resistance to Attrition rating higher than 95%.

SUMMARY OF THE INVENTION

The present invention provides a novel method for the manufacture of improved carrier granules. The method of this invention forms a mixture comprising (A) fibers, (B) mineral filler, and (C) binder. The mixture contains 32-48 weight-% wood fibers having a bulk density of less than 20 pounds per cubic foot, at least 35 weight-% of which fibers are retained on a 50-Mesh U.S. Sieve Series screen. The fibers employed in this invention generally have a moisture content of less than 15 weight-%. The mixture also contains 52-65 weight-% mineral filler having a moisture content of less than 12 weight-%. In addition, the mixture contains 3-7 weight-% binder. The method of this invention agglomerates the mixture by conditioning and agglomerating it in a pin mixer to form small particles followed by agglomerating the mixture in a disc or pan pelletizer to form substantially spherical granules. The method of this invention then dries the granules, generally to a moisture content of less than about 5 weight-%, and screens the granules, to select granules that pass through a 10-Mesh U.S. Sieve Series screen but are retained on a 40-Mesh U.S. Sieve Series screen.

The carrier granules of this invention are substantially free of resins such as urea-formaldehyde resin and of diphenylmethane diisocyanate resin. That is, in the present invention, resins such as diphenylmethane diisocyanate and urea-formaldehyde are not employed to produce a granular substrate which resists degradation during handling. The granules of the present invention depend for their beneficial properties upon their primary fiber and binder ingredients rather than upon any resin derived, for instance, from a source of their fiber component.

A carrier granule embodiment of the present invention contains: 32-48 weight-%, more preferably 38-48 weight-%, of wood fibers having a bulk density of less than 20 pounds per cubic foot, wherein at least 35 weight-% of said fibers are retained on a 50-Mesh U.S. Sieve Series screen; 52-65 weight-%, more preferably 52-62 weight-%, mineral filler; and 3-7 weight-%, more preferably 3-6 weight-%, binder. The mineral filler is preferably kaolin, titanium dioxide, sodium bicarbonate, calcium carbonate, lime, fly ash, dolomite, gypsum, granite fines, or mixtures thereof, and preferably has a particle size range within the range 10 to 500 microns. The binder is preferably granules of superabsorbent polymer, water-soluble starch, acrylic polymer, polyvinyl acetate, guar gum, or mixtures thereof, and at least 70% of the binder granules preferably are sized to pass through a 200-Mesh U.S. Sieve Series screen.

In an embodiment of the present invention which employs granite fines as a filler, the granules may contain 38-48 weight-% of wood fibers having a bulk density of less than 20 pounds per cubic foot, 52-62 weight-% of mineral filler comprising granite fines having a bulk density of less than 75 pounds per cubic foot, and 3-6 weight-% of a starch-based or dextrin-based adhesive binder. These granules have a Resistance to Attrition of at least 90%.

In accordance with this invention, the carrier granule passes through a 10-Mesh U.S. Sieve Series screen and is retained on a 40-Mesh U.S. Sieve Series screen. The granule has a moisture content of less than 5 weight-%. The granule has a resistance to attrition of at least 95%. And the granule has a bulk density of less than 40 pounds per cubic foot, preferably 25-30 pounds per cubic foot.

The carrier granules of this invention may be used, for instance, in pesticidal compositions. Such pesticidal compositions will include a pesticidally effective amount of a pesticide releasably carried on a carrier granule as described above.

BRIEF DESCRIPTION OF THE DRAWINGS

FIG. 1A shows a combination of long and short fibers for use in the present invention.
FIG. 1B shows Medium-Density Fiberboard (MDF) fibers.

DESCRIPTION OF PREFERRED EMBODIMENTS

Figure 2A:
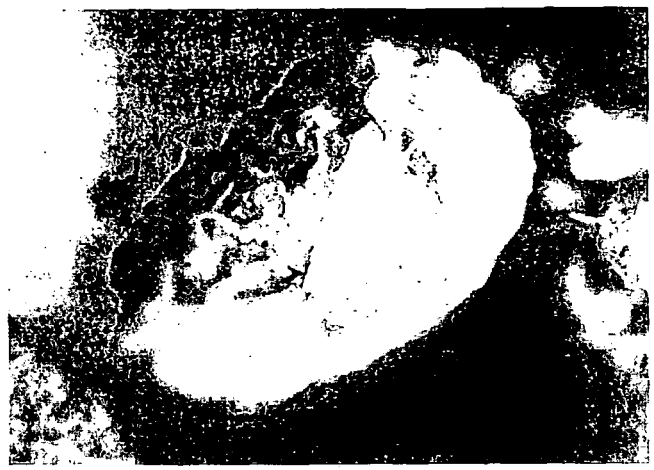
FIG. 2A shows a carrier granule of the present invention.

In the present invention, the wood fibers serve as a structural skeleton for the granules. They also contribute to the formation of cavities (that is, pores) within the granules, thus reducing product weight and improving the release of active chemicals (pesticides, fertilizers, etc.). The fiber size distribution of the wood fibers in the granules will preferably provide a combination of short and long fibers that will contribute to the development of a strong yet open structure in the granules. The dry wood fibers in the granule will generally have a length of up to 2 millimeters, with a minimum of 35% of the fibers being retained on a 50-Mesh U.S. Sieve Series screen. For a tabulation of U.S. Sieve Series screen nomenclature, see Perry's Chemical Engineering Handbook, 6th Ed., McGraw-Hill, Inc., New York, N.Y. (1984), p. 21-15 (Table 21-6). Inasmuch as the median granule size in this invention is approximately 20-Mesh, which=0.841 mm, such fibers are—in the context of this invention and compared to flour-like fibers—"long". The wood fibers preferably have a moisture content of less than 15 weight-%. Long "fluffy" wood fibers which weigh less than 20 pounds per cubic foot are preferred.

Wood fibers usable in accordance with this invention may be made from sawdust and similar waste or by-product of hardwood and softwood manufacturing facilities. Fibers in the wood waste as received vary in length, e.g. from 15 mm to 10 microns. The required size fibers for this invention (from about 10 microns to about 2 mm) are obtained by passing the wood through a hammer mill and employing screening to select out fibers of the desired sizes.

FIGS. 1A and 1B are photographs of two different types of wood fibers. FIG. 1A shows a combination of long and short fibers that can be used in the present invention. The long fibers in FIG. 1A will be retained on a 50-Mesh U.S. Sieve Series screen. FIG. 1B shows Medium-Density Fiberboard (MDF) fibers. These fibers are used in the lumber industry to make high grade plywood-type products; such fibers usually contain urea formaldehyde binder. The MDF fibers are very small, in fact, flour-like. They are not suitable for practicing the preferred embodiments of the present invention.

The mineral in the granule is a filler which gives the granule its desired specific weight. Fillers that may be used include kaolin, titanium dioxide, sodium bicarbonate, calcium carbonate, and mixtures thereof. In a preferred embodiment of the invention, this filler is a lime derivative, e.g., lime itself, fly ash, dolomite, calcium carbonate, gypsum, and mixtures thereof. However, any inert, preferably low pH mineral that has a high specific weight and is capable of supplying fine particles may be. Calcium carbonate or agricultural lime is currently preferred. Generally, the dry mineral filler has a particle size range within the range 10 to 500 microns, and has a moisture content of less than 12 weight-%. Any mineral filler with particles smaller than 30-Mesh U.S. Sieve Series will be operative in the present invention.

Another class of mineral filler that can be used in the present invention is granite fines. Granite fines are available as a by-product from granite quarries and from operations where granite is cut or engraved. Granite fines thus are economical, and their use in the present invention has environmental advantages. The liquid absorption of granite is lower than that of lime or dolomite or calcium carbonate. Accordingly, in agglomeration and palletizing and other such granulation processes that employ moisture, the total amount of water used will be significantly less when granite fines are used as the filler rather than one of the afore-mentioned conventional fillers. This has an impact also on energy costs, since less energy will be needed to dry the granules. Another advantage of granite fines is their low pH. Granules used in cat litter or as carriers for pesticides preferably have low pH, so that often—when using a mineral with a high pH, such as calcium carbonate or lime—a pH buffer or a low pH additive is necessary. Finally, granite fines are chemically stable. In some case, chemical ingredients applied on granules will react with fillers such as calcium carbonate. The use of granite fines as fillers avoids undesired chemical interactions. Typically, the granite fines will have a particle size in the range 10 to 100 microns.

The binder assists the wood fibers in providing structural form to the granules. One or more than one binder material may be used. Binders may be selected from amongst organic binders, synthetic binders, and polymeric binders including superabsorbent polymers. Typical binders that may be used in this invention include starch, acrylic polymer, polyvinyl acetate, guar gum, and mixtures thereof. It is currently preferred to employ a starch that dissolves well in cold water as the binder. More preferably, the binder is constituted of unmodified starch granules, at least 70% of which pass through a 200-Mesh U.S. Sieve Series screen.

Manufacture

To manufacture the granules of this invention, a homogenous granule mixture is prepared and then is pelletized and the pellets are dried and screened. More specifically, this invention contemplates a method for making a granule, which method includes the steps of: forming a mixture comprising 32-48 weight-% dry wood fibers, 52-65 weight-% dry mineral filler, and 3-7 weight-% binder; pelletizing the mixture in a pin mixer and disc or pan pelletizer to form substantially spherical granules; and screening the granules to select granules which, for instance, pass a 10-Mesh U.S. Sieve Series screen but are retained on a 40-Mesh U.S. Sieve Series screen.

Dry Blends Preparation. In this stage, a bulk mixture of components in the desired weight ratios is prepared. Each scheduled component is dosed in its turn from a weighing station into a hopper. Once all of the components are in the hopper, the unmixed batch is conveyed to a mixer. The components, which at this point differ in bulk density and texture, require intensive mixing to achieve a good mix. A typical mixing procedure mixes each batch for from 90 to 120 seconds in a plowshare high-speed mixer. Once well mixed, each batch is conveyed to a surge and combined with other batches having the same component weight ratios.

Agglomeration. This stage creates granules from a dry blend of granule components. Dry blend is dosed continuously into a pin mixer. At the same time, water is injected into the pin mixer at several different locations. High-speed rotation of the wetted blend within the pin mixer creates "seeds" or small particles of the blended materials. During this step, the wood fibers are "conditioned" or softened by the water. This conditioning step is important in the present invention due to our use of long fibers. The wetted blend is then transferred to an agglomeration pan, where agglomeration is completed. In the agglomeration pan, more material accumulates around each seed, and more waters is added, creating a more spherical granule. Parameters such as granule size and weight can be controlled in this stage by changing the blend/water ratio as well as by changing the speed and/or inclination of the pin mixer and/or the agglomeration pan.

Compacting. At this point, the wet granules are compacted in a rotating drum. This imparts their final strength and bulk density characteristics. Variations in strength and/or bulk density can be achieved by adjusting the length of time and/or speed of rotation, following empirical determination of relationships between rotation and those characteristics.

Drying. In this stage, wet granules are dried to reach their final moisture level. The open structure of the granules reduces significantly the drying time and the energy required for drying. Perforated belt dryers or fluidized bed dryers are employed to remove the necessary amount of moisture from each granule. The desired final moisture content, generally from about 2% to about 4%, is achieved by controlling the air temperature, air speed, and granule throughput rate in the dryer.

Dry Screening. Once dried, the batch of granules of this invention may be screened to remove both oversized granules and undersized granules, and to provide a product having a uniform granule size profile. Those skilled in the art are familiar with appropriate screening technology and the use of such devices as vibrating and rolling machines. The oversized and undersized granules are recycled to the Dry Blend Preparation stage.

Figure 2B:
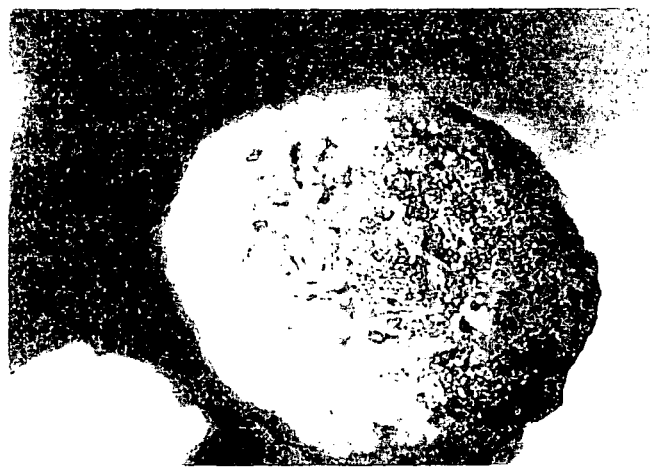
FIG. 2B shows a granule made with MDF fibers.
Figure 2C:
FIG. 2C shows a paper sludge granule.

GRANULES. FIG. 2A shows a granule manufactured in accordance with the present invention. The carrier granule of this invention is coherent in shape, while providing a somewhat open and porous structure. Long fibers can be seen at the surface of this granule. In contrast, FIG. 2B shows a granule made with MDF fibers. FIG. 2C shows a paper sludge granule. The granules of FIGS. 2B and 2C have a dense appearance. They lack openness and porosity of the present invention and are significantly heavier.

PREFERRED WOOD FIBER SOURCES. The wood fiber used in this invention is typically wood fiber generated as a by-product by the furniture industry. At least 80 weight-% of the wood fiber employed in the preferred formulations is from hardwood. Up to 20 weight-% of the wood fiber may be softwood-derived. Urea or formaldehyde are not acceptable, so that a wood component derived from such sources as particleboard (which may contains high percentage of such chemicals) is not employed here. In the preferred formulations of the present invention, the wood fiber as received from the furniture industry is ground in a hammermill and then screened with a #30 Mesh screen. The bulk density of the ground wood fiber is typically in the range 12-16 pounds per cubic foot.

SPECIFIC FORMULATIONS. Typical specific formulations are set forth below. Those skilled in the art will recognize that the specific ingredients recited and their relative amounts can be varied widely while still making available the benefits provided by the present invention.

Quality wood fiber comprising at last 80% hardwood and up to 20% softwood is used as the fiber source. No urea or formaldehydes are included. Particleboard and Medium Density Fiberboard are not acceptable fiber sources in accordance with this invention. The wood fibers are ground in a hammermill and then screened through a No. 30 Mesh screen. The wood fibers provide the granule with a "webbing" which imparts strength and excellent absorption properties to the granules. The bulk density of the ground wood averages between 12 and 16 pounds per cubic foot. A mineral such as calcium carbonate or dolomite or granite fines is used as a filler to provide weight to the finished product. The mineral may have a bulk density in the range of 65 to 75 pounds per cubic foot. The filler mineral will have a moisture content of less than 12% and at least 70% of the mineral particles will pass through a No. 200 Mesh screen. Binder is employed to provide strength and elasticity to the granule. An example of a starch that may be used in this invention is cornstarch. The unmodified starch is heated in water to a temperature of approximately 170° F. to swell and rupture the starch molecules. A typical granule contains 38-48 weight-% wood fiber, 52-62 weight-% mineral, and 3-6 weight-% binder. The finished product has a bulk density of about 26-30 pounds per cubic foot, an ASTM attrition rating of 97% or higher, an internal visual dust test result of 3 seconds, and an angle of repose of 30-39°.

Example # 1

| Components | Weight-% |
| --- | --- |
| Wood Fibers | 40% |
| Calcium Carbonate | 54% |
| Unmodified Starch | 6% |
| Total | 100% |

Example # 2

| Components | Weight-% |
| --- | --- |
| Wood Fibers | 35% |
| Calcium Carbonate | 60% |
| Unmodified Starch | 5% |
| Total | 100% |

Examples # 3 and # 4

In these Examples, various test procedures are used to determine significant properties of the carrier granules. The carrier granules tested are made of hardwood fibers, calcium carbonate, and binder. They differ with respect to their granule size profiles. ASTM E727-02 is entitled "Test Methods for Determining Bulk Density of Granular Carriers and Granular Pesticides". ASTM E728-91 is entitled "Standard Test Method for Resistance to Attrition of Granular Carriers and Granular Pesticides". ASTM E1521-98 is entitled "Test Method for Liquid Holding Capacity of Granular Carriers". ISO 8398-89 is entitled "Solid Fertilizers—Measurement of Static Angle of Repose". The procedures for carrying out these standard tests are expressly incorporated by reference herein.

| 14/40 Mesh | | |
|---|---|---|
| Bulk density | ASTM E727-01 | 27.5 lbs/ft$^3$ |
| Resistance to attrition | ASTM E728-91 | 95% |
| Liquid holding capacity | ASTM E1521-98 | 25% |
| Angle of repose | ISO 8398-89 | 39.0° |
| Moisture content | | 1-2% |
| pH | | 7-8 |
| Visual dust* | | 2-3 seconds |
| 10/14 Mesh | | |
| Bulk density | ASTM E727-01 | 28.0 lbs/ft$^3$ |
| Resistance to attrition | ASTM E728-91 | 98% |
| Liquid holding capacity | ASTM E1521-98 | 27% |
| Angle of repose | ISO 8398-89 | 39.5° |
| Moisture content | | 1-2% |
| pH | | 7-8 |
| Visual dust* | | 2-3 seconds |

*The "visual dust" determination is a visual determination of airborne dust.

The time given is the time it takes for virtually all of the dust to dissipate in the following procedure. 3 liters of product are placed in a tray and poured from a height of 14 inches into another tray, at a constant flow rate that pours out all of the product in 6-8 seconds. Once the sample has been completely poured out, a stopwatch is activated. When all of the dust has settled, the stopwatch is stopped and the time necessary for all of the dust to settle. This measurement, of the number of seconds required for the dust to dissipate, indicated the relative dustiness of the sample.

Example # 5

Use as a Carrier 100 pounds of granules of Example 1 and 5 pounds of carbaryl (Sevin) pesticide dispersed in 10 gallons of water are dosed in turn from a weighing station into a hopper. The unmixed batch is conveyed to a plowshare high-speed mixer, where they are mixed for from 90 to 120 seconds in a plowshare high-speed mixer to provide a product that can be used to deliver the carbaryl pesticide to lawns.

What is claimed is:

1. A lightweight carrier granule comprising
   32-48 weight-% of wood fibers having a bulk density of less than 20 pounds per cubic foot, wherein said wood fibers range from 10 microns to 2 millimeters in length and at least 35 weight-% of said fibers are retained on a 50-Mesh U.S. Sieve Series screen,
   52-65 weight-% mineral filler having a particle size range within the range 10 to 500 microns, and
   3-7 weight-% binder,
   wherein said granule passes through a 10-Mesh U.S. Sieve Series screen and is retained on a 40-Mesh U.S. Sieve Series screen, said granule has a moisture content of less than 5 weight-%, said granule has a Resistance to Attrition of at least 95%, and said granule has a bulk density of 26 to 30 pounds per cubic foot.

2. The lightweight carrier granule of claim 1, wherein said wood fibers are derived from a source that does not contain urea-formaldehyde resin or diphenylmethane diisocyanate resin.

3. The lightweight carrier granule of claim 1, wherein the mineral filler is selected from the group consisting of kaolin, titanium dioxide, sodium bicarbonate, calcium carbonate, lime, fly ash, dolomite, gypsum, granite fines, and mixtures thereof.

4. The lightweight carrier granule of claim 1, wherein the binder is selected from the group consisting of granules of superabsorbent polymer, water-soluble starch, acrylic polymer, polyvinyl acetate, guar, gum, and mixtures thereof, and wherein at least 70% of the binder granules pass through a 200-Mesh U.S. Sieve Series screen.

5. The lightweight carrier granule of claim 1, comprising 38-48 weight-% of wood fibers at least 35 weight-% of which are retained on a 50-Mesh U.S. Sieve Series screen, 52-62 weight-% carbonate or dolomite or granite fines having a bulk calcium density of 65-75 pounds per cubic foot, and 3-6 weight unmodified starch binder, said granule having a bulk density of 26-30 pounds per cubic foot.

6. The lightweight carrier granule of claim 1 comprising 38-48 weight-% of wood fibers having a bulk density of less than 20 pounds per cubic foot, 52-62 weight-% of mineral filler comprising granite fines having a bulk density of less than 75 pounds per cubic foot, and 3-6 weight-% of a starch-based dextrin-based adhesive binder.

7. The lightweight carrier granule of claim 6, wherein the granite fines have a particle size in the range 10 to 100 microns.

8. The lightweight carrier granule of claim 1, comprising 40 weight-% wood fibers, 54 weight-% calcium carbonate filler, and 6 weight-% unmodified starch, binder.

9. The lightweight carrier granule of claim 1, comprising 35 weight-% wood fibers, 60 weight-% calcium carbonate filler, and 5 weight-% unmodified starch binder.

* * * * *